United States Patent [19]

Boon et al.

[11] Patent Number: 5,306,809
[45] Date of Patent: Apr. 26, 1994

[54] ACID-LABILE LINKER MOLECULES

[75] Inventors: Petrus J. Boon, Oss; Franciscus M. Kaspersen, Heesch; Ebo S. Bos, Oss, all of Netherlands

[73] Assignee: Akzo N.V., Arnhem, Netherlands

[21] Appl. No.: 815,671

[22] Filed: Dec. 31, 1991

[30] Foreign Application Priority Data

Dec. 31, 1990 [EP] European Pat. Off. ........ 90203526.0

[51] Int. Cl.$^5$ .................... A61K 35/14; C07K 3/06
[52] U.S. Cl. .................... 530/363; 549/253; 549/332; 549/264; 530/391.9; 530/405; 530/409; 536/6.4; 536/22.1
[58] Field of Search ........ 549/253, 332, 264; 530/363, 391.9, 409, 405; 536/22, 6.4, 22.1

[56] References Cited

U.S. PATENT DOCUMENTS

| | | | |
|---|---|---|---|
| 4,631,190 | 12/1986 | Shen et al. | 424/85 |
| 4,997,913 | 3/1991 | Hellstrom et al. | 530/389 |
| 5,140,013 | 8/1992 | Gaudreault et al. | 530/409 |

FOREIGN PATENT DOCUMENTS

WO8601409 3/1986 World Int. Prop. O. .

OTHER PUBLICATIONS

Y. Liwschitz, et al., J. Chem. Soc. ©1968, 1843-5.
H. O. House, *Modern Synthetic Reactions,* pp. 132-133, 156-159. W. A. Benjamin; N.Y., N.Y. (1965).

*Primary Examiner*—Michael G. Wityshyn
*Assistant Examiner*—C. Sayala
*Attorney, Agent, or Firm*—William M. Blackstone; Mary E. Gormley

[57] ABSTRACT

This invention relates to the field of immune therapy of cancer, more specifically to immunoconjugates of a cytotoxic moiety with a targeting moiety, more specifically to immunoconjugates of antibodies or fragments or functional derivatives of antibodies coupled to a cytotoxic substance such as drugs, toxins or radioisotopes. It especially relates to the release of substances bound to a targeting moiety through the use of acid-cleavable linker molecules.

24 Claims, 6 Drawing Sheets

ACID-LABILE LINKER MOLECULES

FIELD OF THE INVENTION

This invention relates to the field of immune therapy of cancer, more specifically to immunoconjugates of a cytotoxic moiety with a targeting moiety, more specifically to immunoconjugates of antibodies or fragments or functional derivatives of antibodies coupled to a cytotoxic substance such as drugs, toxins or radioisotopes. It especially relates to the release of substances bound to a targeting moiety through the use of acid-cleavable linker molecules.

BACKGROUND OF THE INVENTION

Immunotherapy is already an often suggested treatment modality in the field of cancer therapy. With the targeting possibility of antibodies or members of a specific binding pair a much more precise localization of the active compounds can be achieved, while at the same time the overall dose of the active compound can be lowered, thereby reducing the general detrimental effects. In early attempts (monoclonal) antibodies or other targeting moieties have been loaded directly with radioactive elements such as $^{67}$Ga, $^{131}$I, $^{99m}$Tc, $^{111}$In or other isotopes (e.g. Marchalonis J.J., Biochem. J. 113, 299–305, 1969). In a later study coupling of isotopes to antibodies has been achieved by using chelating agents such as EDTA (Krejcarek and Tucker, Biochem. Biophys. Res. Commun. 77, 581–585, 1977) or DTPA (U.S. Pat. No. 4,454,106).

The use of drugs or toxins has also been suggested. The coupling of drugs or toxins to the antibody or to a carrier loaded with one or more antibodies has to be performed through a linking agent, although it is also possible to make recombinant fusion proteins of toxins and/or carriers and targeting moiety.

Linking agents are well known and a considerable range of these reagents is available. In broad terms, a linking reagent comprises two or more reactive functional groups covalently linked together, such as carbohydroxy-, amino-, thio- or sulfhydryl-groups. The covalent linkage between the two functional groups may be direct, but in many cases the reactive functional groups are separated by respective covalent attachment to a bridging group or spacer. The reactive functional groups may be the same or different. Different groups are to be preferred because they allow a more controlled coupling.

The chemical structure of the linker determines the ability of the active compound to be released and to express its activity at the target site. Initially, peptidic linker structures were applied, which were susceptible to cleavage by lysosomal enzymes (Trouet et al., Proc. Natl. Acad. Sci. 79, 626–629, 1982). This approach requires internalization of the conjugates following binding to the target cell. In the target cell the lysosomal enzymes release the active compound from the targeting molecule.

Another development is a linker structure based on aconitic acid, in order to attach amino group containing drugs through an acid labile amide bond (Shen and Ryser, Biochem. Biophys. Res. Comm. 102, 1048–1054, 1981). Here again effective release of the drug requires transport of the conjugates to intracellular, acidic organelles such as endosomes and lysosomes (De Duve et al., Eur. J. Biochem. 137, 391–397, 1983).

The same holds true for U.S. Pat. No. 4,618,492 which describes the use of amino-sulfhydryl linking reagents characterised by the ability to hydrolyse in mildly acidic solutions.

For the application of such a linker, the conjugate has to be internalized. However, only a minor part of the antibodies produced against tumour-associated antigens are able to induce internalization of the immune complex and thus of the active compound attached. This is especially true when the size of the conjugate is increased by the presence of a carrier.

This failure to induce internalization is a major drawback in the use of immunoconjugates in the field of cancer therapy.

SUMMARY OF THE INVENTION

We have discovered a class of linking reagents that permit controlled release of biologically active substances under neutral (also meant to include physiological pH) or mildly acidic conditions. These linkers permit the release of the cytotoxic substance in the immediate vicinity of the target, thereby overcoming the necessity for internalizing targeting moieties, although the linkers of the invention are also suitable for internalizing targeting moieties.

In general these linking reagents comprise maleic acid anhydride derivatives:

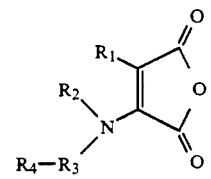

wherein $R_1$ is H, lower alkyl, lower alkylene, lower aryl or aralkyl or these coupled with a divalent organic —O—, —S— or

linking moiety; wherein $R_2$ is H, alkyl, aryl or aralkyl, $R_3$ is

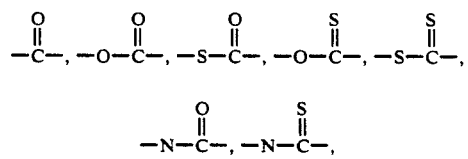

or another chemical structure which is able to delocalize the lone pair electrons of the adjacent nitrogen and $R_4$ is a pendant reactive group, capable of linking $R_3$ to a carrier molecule, a proteinaceous substance, an antibody (fragment), a polymer or a nucleic acid.

Another embodiment comprises the conjugate:

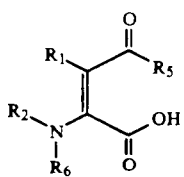

wherein $R_1$, $R_2$ and $R_3$ are as defined above and wherein $R_5$ is the acylated active substance and $R_6$ is $R_3$ coupled with the carrier, proteinaceous substance, antibody (fragment) polymer or nucleic acid. Also included are the following compounds according to:

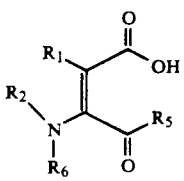

wherein all groups are as defined above.

Mixtures of conjugates as described above are also included.

The advantage of the invention lies in the fact that the above described compounds can be hydrolysed at neutral or very mildly acidic pH-values. Because there is a neutral or mildly acidic environment in tumour tissue, this enables cleavage of the conjugates in the immediate vicinity of tumour cells, thereby circumventing the necessity of internalisation of the conjugate. This means that the conjugates can be made not only with antibodies but with any targeting moiety that is able to recognize specific markers on the cells or structures to which the conjugates are targeted. Thus it is possible to use nucleic acids, carrier molecules, proteinaceous substances, polymers or any kind of members of specific binding pairs.

Therefore another therapeutic area for these conjugates is killing of a specific population of cells, e.g. T-cells in auto-immune diseases.

Another advantage of the release of the active compounds in the immediate environment of the target cell is that the compounds may also act on adjacent malignant cells on which the recognition site for the targeting moiety is not present.

Yet another advantage of the above described linker molecules lies in the fact that the sensitivity to (acidic) cleavage can be changed by varying the size and/or the nature of the substituents at $R_1$ and/or $R_2$ or the maleamic acid moiety. In general it can be said that the bulkier the substituents the more labile the conjugate will be. This property gives the opportunity to tailor the conjugates to specific requirements. First of all it is possible to account for the time needed for the targeting moiety to localize at the target cells as well as for the residence time at said cells.

Secondly in this way a controlled release of the active compound can be achieved which can be adjusted to a) the specific environment of the target cells, b) the rate of clearance of the unbound conjugates and c) the type of active compound used. This last item is especially useful knowing that the size and the pKa of the active compounds to be used may change the susceptibility to cleavage from the conjugates. Therefore it is possible to generate a conjugate that will release any particular active compound in the desired pH-region.

The stability of the conjugate in normal serum (pH 7.4) is such that cleavage of the linker occurs with a $T_{\frac{1}{2}}$ of several days, so that unbound conjugates have been cleared from the serum before a detrimental amount of the cytotoxic compounds has been generated. The above described linking compounds are useful for crosslinking molecules, such as proteins, for example antibodies or antibody fragments or functional derivatives of antibodies, or other members of specific binding pairs, such as ligands or peptide hormones, or receptor binding fragments or derivatives thereof, especially for cell surface receptors; to effector molecules such as cytotoxic drugs, toxins, metalloproteins, chelates with (radioactive) metals, or to other proteins, carbohydrates, nucleic acids or other biological effective molecules, to form conjugates for use in diagnosis or therapy in vivo or in vitro.

The preferred targeting moiety is a molecule specific for a tumour cell, such as antibodies or antibody fragments targeted against antigens such as CEA, AFP, BFP, hCG, $\uparrow_2$-microglobulin or other tumour markers, or targeted against antigens or antibodies related to viruses as HBsAg, HBeAg, anti-HBs, NANBV, retroviruses as HTLV or FeLV.

The preferred active substance to be delivered is a cytotoxic drug. Particularly preferred, the active substance is a drug which has a chemical moiety which can be acylated, e.g. an amine-, hydrazide-, phenolic hydroxy-, thio- or mercapto-group, such as adriamycin, daunomycin, mitomycin C, verrucarin A or other trichothencenes, methotrexate, 5-fluorouracil or derivatives, cytarabine, pentostatin, vincristine or other vinca-alkaloids, etoposide, teniposide, dactinomycin, mitoxantrone, bleomycin or any other cytotoxic substance.

For a given conjugate, one skilled in the art will recognize that an estimate can be made of release rates of the drug and the yield of free drug at the target site for a range of pH and temperature conditions that are encountered in vivo. On that basis a calculation can be made of the amount of conjugate necessary for a substantial cytotoxic effect on the target cells.

The invention is further characterized in the following examples:

EXAMPLES.

EXAMPLE 1

Preparation of a bifunctional linker reagent

A bifunctional reagent that serves to introduce a labile maleamic acid structure was prepared as depicted in scheme 1.

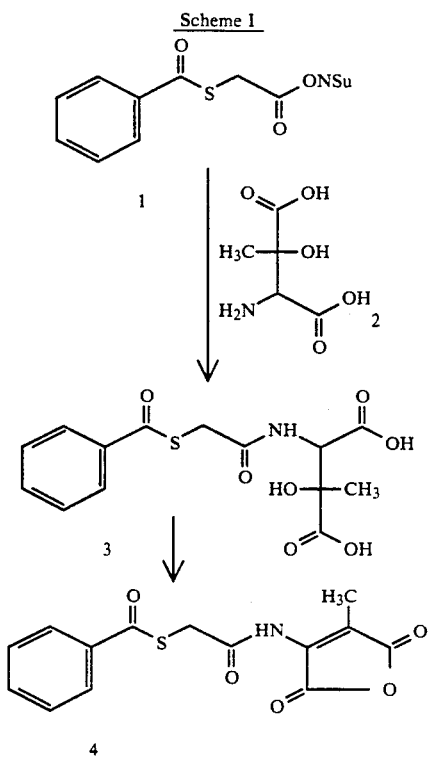

1. Preparation of N-succinimidyl, S-Benzoyl-mercaptoacetate (1)

1. S-Benzoyl-mercaptoacetic acid (4.6 g; 23.4 mmoles), prepared according to the procedure described by R.F. Schneider et al. (J.Nucl.Medicine 25, 223-229, 1984), and N-hydroxysuccinimide (2.7 g; 23.4 mmoles) were dissolved in dichloromethane (50 ml). The solution was cooled at −10° C., upon which dicyclohexylcarbodiimide (4.86 g; 23.6 mmoles) was added. The mixture was stirred at −10° C. for 1 hour and then kept at 4° C. for 16 hours. Precipitated dicyclohexylurea was filtered off, and the filtrate was evaporated in vacuo. The solid residue was triturated with ethyl acetate-ether (1:1), filtered, washed with ether and subsequently dried in vacuo to give the title compound 1 (4.0 g; 13.6 mmoles; 58%).

$^1$H-NMR (d$^6$DMSO):
2.82 ppm (S,4H, —CO—CH$_2$—CH$_2$—CO—);
4.45 ppm (S,2H, —S—CH$_2$—CO—);
7.6-8.0 ppm (m,5H, arom).

2. Preparation of β-hydroxy, β-methyl-aspartic acid (2)

Compound 2 was prepared from pyruvic acid and copper-glycinate according to the procedure described by L. Benoiton et al. (J.Am.Chem.Soc. 81, 1726-1729, 1959).

3. Preparation of N-(S-Benzoylmercapto acetyl)-β-hydroxy, β-methyl-aspartic acid (3)

3. Compound 1 (0.58 g; 2.0 mmoles) was dissolved in dimethylformamide (DMF) (5.0 ml). β-Hydroxy, β-methyl-aspartic acid (0.32 g; 2 mmoles) and triethylamine (0.28 ml) were subsequently added to the DMF solution. A clear mixture was obtained within 15 minutes. The mixture was stirred for 5 hours. A few drops of acetic acid were added and the solvent was removed in vacuo. The residue was dissolved in aqueous potassium bisulfate (2% w/w) solution (10 ml). The product was then extracted from the aqueous solution with sec-butanol-dichloromethane (2:3, v/v; 3 times, 10 ml each).

The organic phase was washed once with saturated sodium chloride solution and dried on sodium sulfate. The solvents were removed in vacuo and the residue was purified by chromatography on silica-60 (Merck, 40-63 μm) using the solvent system butanol-1-acetic acid-water (4:1:1; v/v) to give compound 3 (0.44 g; 64%).

$^1$H-NMR (CD$_3$OD): 1.38 ppm (s, CH$_3$) and 1.50 ppm (s, CH$_3$) (ratio erythro:threo∼1:1; sum:3H) 3.88-4.00 ppm (m, 1H, —NH—C̲H̲—CO—) 4.87 ppm (s, 2H, —S—CH$_2$—CO—); 7.48-8.02 (m, 5H, arom.).

4. Preparation of 2-N-(S-Benzoylmercapto acetyl)amino, 3-methyl-maleic acid anhydride (4)

4. Aspartic acid derivative 3 (0.20 g; 0.58 mmoles) was dissolved in acetic anhydride (2.0 ml). The solution was kept at 100° C. for 20 minutes. Subsequently the solvent was evaporated in vacuo to give a solid residue, that was triturated with ether-hexane (1:1; v/v), filtered off and dried in vacuo to give the pure title compound 4 (0.092 g; 52%).

$^1$H-NMR (CDCl$_3$):

2.23 ppm (s, 3H, CH$_3$), 3.89 ppm (s, 2H, —S—CH$_2$—CO—); 7.46-8.05 (m, 5H, arom.) 8.75 ppm (br.s, 1H, NH).

EXAMPLE 2

Derivatization of adriamycin with the bifunctional linker reagent 4. (Scheme II)

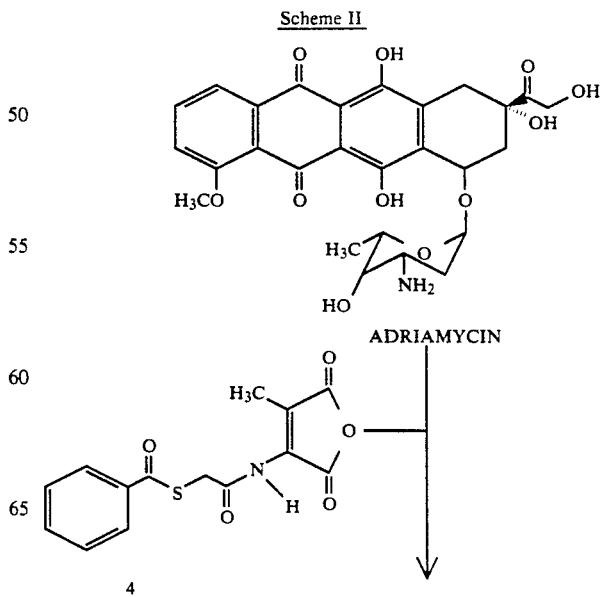

-continued
Scheme II

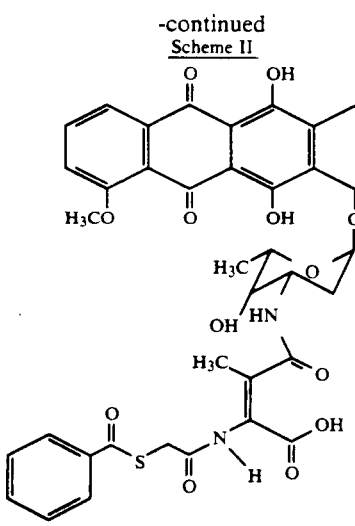

Adriamycin.HCl (66 mg; 0.11 mmoles) was suspended in DMF (1.0 ml). Maleic anhydride derivative 4 (39 mg; 0.13 mmoles) and ethyl,diisorpopylamine (63 μl; 0.36 mmoles) were successively added. A clear solution was obtained within 5 minutes. TLC (silica; Merck) in the solvent system dichloromethane-methanol-water-triethylamine (70:30:5:0.1; v/v) indicated complete conversion of adriamycin. The reaction mixture was added dropwise to cold ethyl acetate (30 ml) while stirring, upon which the products precipitated. The precipitate was isolated by centrifugation and subsequently washed 3 times with ethyl acetate and finally with ether and dried (56 mg; 58%).

$^1$H-NMR (DMSO, D$^6$) confirmed the presence of the linker structure and indicated the two possible isomeric structures, products of reaction of the adriamycin amine function at either the C$^1$ or the C$^4$ carbonyl position of the maleic anhydride reagent (see scheme II), to be present in approximately equal amounts.

The two isomeric products were clearly separated during hplc analysis on a Bondapak-C18 column (see FIG. 1A): with isocratic elution using the solvent systeem A:B=92:8 v/v, where A=methanol-water (3:2, v/v), containing 0.3% (w/v) of ammonium acetate, and B=methanol, at a flow of 1.0 ml/min and detection at 254 nm.

|  | Rt |
| --- | --- |
| Adriamycin: | 9.8 min |
| isomer 1: | 11.0 min |
| isomer 2: | 15.5 min |

EXAMPLE 3 pH-dependent release of adriamycin from its linker-derivative.

The rate of release of adriamycin from the linker derivative was studied at various pH's ranging from 5.0–7.5. A stock solution (10 mg/ml) of the compound described in Example 2 was prepared. Aliquots from this solution were diluted with 50 mM sodium phosphate buffer of pH 5.0, 6.0, 6.5, 7.0 and 7.5, respectively, to a concentration of 0.1 mg/ml. At various times, up to 24 hours, samples were subjected to hplc analysis. Examples of such analyses, at pH 6.5 and 7.0, are presented in FIG. 2.

As shown in FIG. 1B, the rate of release of adriamycin is pH-dependent, being acid catalyzed. From FIG. 2 it is also concluded that the sensitivity to hydrolysis is qualitatively equal for both isomeric linker-derivatives. It is also apparent that quantitative release of adriamycin from the linker-derivatives is attained in time.

EXAMPLE 4

Conjugation of the adriamycin-linker derivative to human serum albumin (HSA) (scheme III).

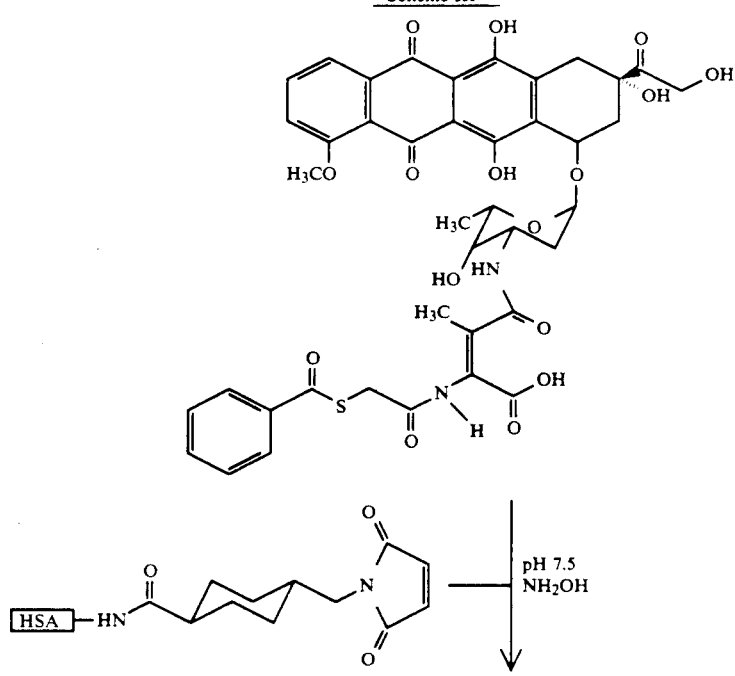

Scheme III

Scheme III -continued

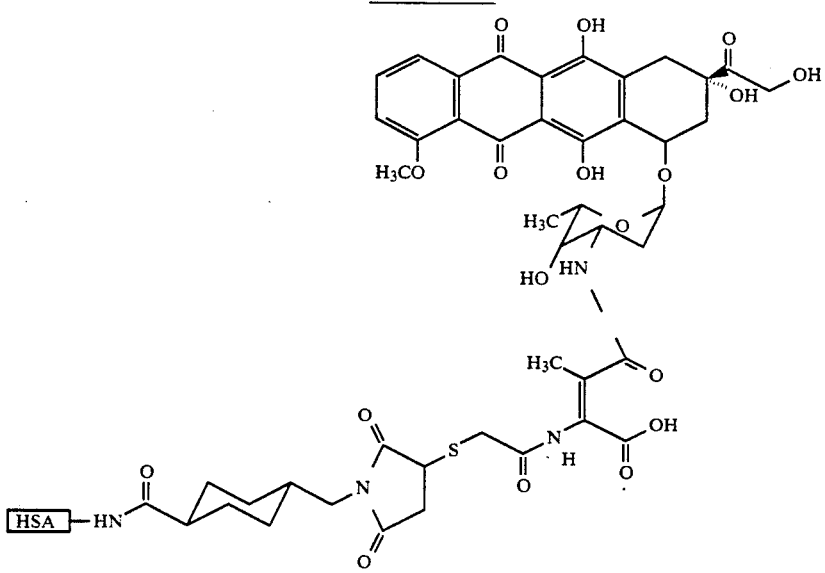

A: Maleoylation of HSA

A freshly prepared solution of N-succinimidyl-4-(N-maleimidomethyl)-cyclohexane-1-carboxylate (SMCC) (2.0 mg) in DMF (0.4 ml) was added to a stirred solution (2.0 ml) of HSA (10 mg/ml) in 50 mM soidum phosphate buffer, pH 7.5.

The mixture was stirred for 30 minutes and subsequently filtered through a column of Sephadex G-25 (PD-10), that was equilibrated and eluted with 50 mM sodium phosphate buffer, pH 7.5. The protein concentration (7.3 mg/ml) of the HSA-fraction was determined by the method of Lowry.

The concentration of maleimido-groups was determined by reacting these functions with a known excess of cysteamine and subsequent spectrophotometric determination of the amount of cysteamine remaining upon reaction with 2,2'-dithiodipyridine according to the procedure of D.R. Grassetti et al., Arch.Biochem. Biophys. 119, 41–49, 1967.

B. Conjugation of adriamycin-derivative to HSA

A solution of adriamycin-linker derivative (1.5 mg), described in Example 2, in dimethylformamide (0.5 ml) was added to 1.3 ml of the maleoylated HSA, obtained as described under A. 0.5 M hydroxylamine (0.072 ml), buffered at pH 7.0, was added to the stirred mixture. The solution was kept at room temperature for 15 minutes and then for 15 hours at 4° C.

A 20 mM solution of cysteamine (0.10 ml), buffered at pH 7.5, was added. After 15 minutes the solution was applied to a Sephadex LH-20 column, equilibrated and eluted with 50 mM sodium phosphate buffer -DMF (2:1; v/v), at pH 7.5. The protein containing eluate was collected and filtered through a column of Sephadex G-25, that was eluted with 50 mM sodium phosphate buffer, pH 7.5. The amount of HSA was determined by the Lowry method. The amount of adriamycin bound to the HSA was determined spectrophotometrically. ($\epsilon M_{487}=9000$). The substitution ratio was found to be 3.7 moles of adriamycin per mole of HSA.

EXAMPLE 5

Preparation of a bifunctional linker reagent

A bifunctional reagent, differing from compound 4 (scheme I) by the substitution of the mercaptobenzoyl for the mercaptoacetyl function, was prepared as depicted in scheme IV.

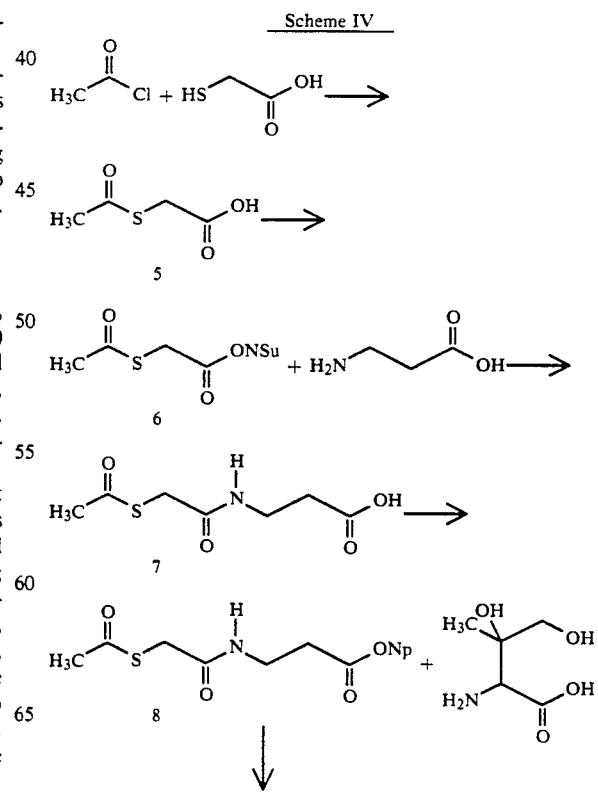

-continued
Scheme IV

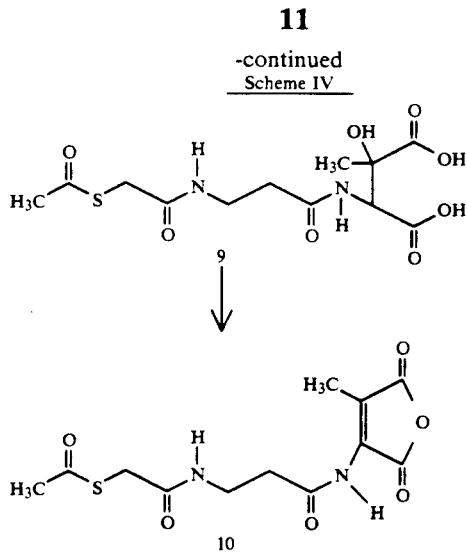

1. Preparation of S-acetyl-mercaptoacetic acid (5)

Acetylchloride (175 ml) was slowly added to mercapto-acetic acid (100 ml). The mixture was heated at reflux temperature for 1 hour. Subsequent distillation in vacuo afforded the pure title compound (84.1 g).

$^1$H-NMR (CDCl$_3$):2.41 ppm (s,3H); 3.74 ppm (s,2H).

2. Preparation of N-succinimidyl,S-acetyl-mercaptoacetate 6

Compound 5 (84 g; 0.62 mole) and N-hydroxysuccinimide (72 g; 0.62 mole) were dissolved in dichloromethane (600 ml). The solution was cooled to 0° C., whereupon dicyclohexylcarbodiimide (129.8 g; 0.627 mole) was added. The mixture was stirred at 0° C. for 1 hour and for another 20 hours at room temperature. Following cooling of the mixture at 0° C., the precipitate of dicyclohexylurea was filtered off. The filtrate was evaporated in vacuo to leave a solid residue. The product was triturated with propanol-2 (400 ml) at 0° C. and subsequently isolated by filtration. Crystalline 6 was obtained in 92.5% yield (134.2 g).

$^1$H-NMR (CDCl$_3$): 2.43 ppm (s,3H); 2.85 ppm (s,4H); 3.98 ppm (s,2H).

3. Preparation of N-(S-acetylmercaptoacetyl)-β-alanine 7

To a solution of β-alanine (24.36 g; 0.27 mole) in water (300 ml), a 20% (v/v) solution of ethyldiisopropylamine in dimethylformamide was added until the pH was at 8.5. Following dilution of the mixture with dimethylformamide (100 ml) a solution of compound 6 (60 g; 0.20 mole) in dimethylformamide (200 ml) was slowly (30 minutes) added to the stirred reaction mixture, while the pH of the solution was maintained at 6.5-7.0 by simultaneous addition of ethyldiisopropylamine (20% v/v in DMF). The mixture was stirred for 1 hour at room temperature. The pH of the solution was adjusted to 1-2 by addition of 5% (w/w) aqueous potassium bisulfite, whereupon the product was extracted with dichloromethane-butanol-2 (3:2, v/v; 4 times 250 ml). The combined organic layers were washed twice with a saturated sodium-chloride solution and subsequently with water. The solvents were removed by evaporation in vacuo. The residue was dissolved in dichloromethane. The solution was dried on sodiumsulfate. Following removal of inorganic salts by filtration, the solvent was evaporated in vacuo to afford the title compound as a solid (53.8 g) consisting of an approximate 1:1 mixture of the title compound 7 (0.19 mole; 74%) and dimethylformamide.

$^1$H-NMR (CDCl$_3$): 2.40 ppm (s,3H); 2.56 ppm (t,2H;—CH$_2$—CO—O); 3.50 ppm (q,2H;—NH—CH$_2$—CH$_2$—); 3.58 ppm (s,2H;—S—CH$_2$—CO); 7.01 ppm (broad t, 1H; —NH—CH$_2$—).

4. Preparation of the p-nitrophenyl ester derivative of N-(S-acetylmercaptoacetyl)-β-alanine 8.

Compound 7 (22.0 g; 0.107 mole) and p-nitrophenol (14.95 g) were dissolved in dichloromethane. The solution was cooled at −5° C., upon which cicyclohexylcarbodiimide (24.46 g) was added. The mixture was stirred at −5° C. for 30 minutes and was then allowed to warm to room temperature for 2 hours. The mixture was cooled to −5° C. Precipitated dicyclohexylurea was removed by filtration. The filtrate was evaporated in vacuo to leave a residue that spontaneously crystallized. The solid was triturated with diiso-propylether, filtered, washed thrice with diisorpopylether-ethyl acetate (2:1 v/v) and then dried in vacuo to yield the homogenous title compound (18.6 g).

$^1$H-NMR (CDCl$_3$): 2.37 ppm (s, 3H, CH$_3$); 2.86 ppm (t,2H,—CH$_2$—CO—O—); 3,54 ppm (s,2H,—S—CH$_2$—CO—); 3.62 ppm (q,2H,—NH—CH$_2$—CH$_2$—); 6.78 ppm (broad t,1H,—NH—); 7.33 ppm (d,2H,arom); 8.30 ppm (d,2H,arom).

5. Preparation of N-(S-acetyl-mercaptoacetyl)-β-hydroxy,β-methoxy)-aspartic acid 9.

Compound 8 (1.0 g; 3.07 mmoles) was dissolved in dimethylformamide (7 ml). β-Hydroxy,β-methyl-aspartic acid (0.5 g; 3.07 mmoles) was added to the solution. Triethylamine (0.64 ml; 4.5 mmoles) was added to the stirred suspension. Stirring was continued for 2.5 hours, after which a clear solution was obtained. The solvent was then evaporated in vacuo. The residue was dissolved in water and the aqueous solution was subsequently extracted three times with ethyl acetate in order to remove the p-nitrophenol. Following acidification of the aqueous solution to pH 1-2 by addition of 5% (w/w) aqueous potassium bisulfate, the solution was extracted four times with dichloromethane-butanol-2 (3:2; v/v). The combined organic extracts were evaporated in vacuo to give compound 9 as a syrup. The product was purified by column chromatography on silica$^{(R)}$ ("Merck" 40–63 μm) using butanol-1-acetic acid-water (4:1:1; v/v) as the eluent. Fractions containing pure 9 were combined and evaporated in vacuo. The residue was dissolved in water upon which the product was isolated by lyophilization (450 mg; 42%).

$^1$H-NMR (DMSO, D$^6$): 1.30 ppm (s,3H,CH$_3$); 2.32 ppm (t,2H,—CH$_2$—CH$_2$—CO—); 2.37 ppm (s,3H,CH$_3$—CO—); 3.24 ppm (q,2H,—NH—CH$_2$—CH$_2$—); 3.58 ppm (s,2H,—S—CH$_2$—CO—); 4.57 ppm (d,1H,—NH—CH—COOH); 7.98 ppm (d,1H,—NH—CH—COOH); 8.04 ppm (t,1H,—NH—CH$_2$—CH$_2$—).

6. Preparation of 6-(N-(S-acetyl-mercaptoacetyl)-β-alanyl)amino,3-methyl,maleic acid anhydride 10.

Compound 9 (0.284 g) was dissolved in freshly distilled acetic anhydride (4.0 mg). The solution was kept at 100° C. for 15 minutes. Subsequently the solvent was evaporated in vacuo to give a syrup, that was stirred with diethylether-hexane (1:1; v/v). The solvents were removed by decantation, upon which the oil was dried in vacuo (0.256 g).

$^1$H-NMR (DMSO, D$^6$): 2.01 ppm (s,3H,CH$_3$—); 2.37 ppm (s,3H,CH$_3$—CO); 2.65 ppm (t,2H,—CH$_2$—CH$_2$—CO); 3.32 ppm (q,2H,—NH—CH$_2$—CH$_2$—); 3.58 ppm (s,2H,—S—CH2—CO); 8.22 (t,1H,—N<u>H</u>—CH2—); 10.8 ppm (very broad s,1H,—<u>NH</u>—C).

EXAMPLE 6

7. Preparation of analogues of the bifunctional linker reagent 10.

Bifunctional reagents, differing from compound 10 i the substituent at the 3-position of the maleic acid anhydride system were prepared as depicted in Scheme V.

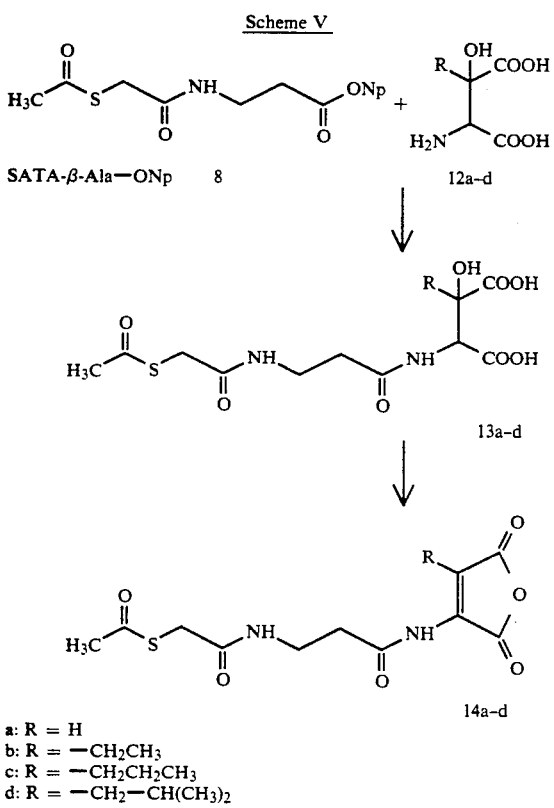

a: R = H
b: R = —CH2CH3
c: R = —CH2CH2CH3
d: R = —CH2—CH(CH3)2

These synthesis were carried out in a manner analogous to that described for reagent 10.

β-hydroxy, aspartic acid derviatives 12b-d were prepared from copperglycinate and 2-oxobutanoic acid, 2-oxopentanoic acid and 4-methyl,2-oxopentanoic acid, respectively, according to the procedure described by L. Benoiton et al. (J. Am. Chem. Soc, 81, 1726-1729, 1959). β-Hydroxyaspartic acid was obtained from Sigma Chem. Comp.

Thin layer chromatography (TLC) was performed on precoated plates of silica gel 60 F254 ('Merck') using the solvent system butanol-1:acetic acid:water=4:1:1. NMR spectra were recorded on a Bruker 200 MHz FT spectrometer. Chemical shifts are reported as δ values (parts per million) relative to tetramethylsilane as an internal reference. Positive ion FAB mass spectra were obtained using a Finigan MAT 90 reverse geometry mass spectrometer.

A: 2-[N-(S-Acetyl-mercaptoacetyl)-β-alanyl]amino maleic acid anhydride 14a.

SATA-β-Ala-ONP 8 (0.50 g, 1.53 mmoles) and β-hydroxyaspartic acid (0.228 g, 1,53 mmoles) were allowed to react in dimethylformamide solution (4 ml) in the presence of triethylamine (0.43 ml, 3.06 mmoles) for 16 hours at ambient temperature. The reaction product 13a was isolated and purified as described for compound 9. The yield was 0.22 g (43%). TLC: Rf=0.18.

1H-NMR (6d-DMSO, δ in ppm): 2.32 (t,2H, —CH-2—CH2—CO—); 2.37 (s, 3H, CH3—CO—); 3.25 (q, 2H, —<u>NH</u>—CH2—CH2—); 3.58 (s, 2H, —S—CH-2—CO—); 4.37 (d, 1H, —CHOH—COOH); 4.66 and 4.71 (dd, sum 1H, —NH—<u>CH</u>—COOH); 7.96 (d, 1H, —NH—CH—COOH); 8.80 (t, 1H, —<u>NH</u>—CH-2—CH2—).

Compound 13a (0.206 g) was dissolved in freshly distilled acetic anhydride (3 mil). The solution was kept at 100° C. for 30 minutes. The solvent was then evaporated in vacuo to give a syrup. Residual acetic anhydride was removed through coevaporation (thrice) with toluene in vacuo. Yield was quantitative.

1H-NMR (6d-DMOS, δ in ppm): 2.35 (s, 3H, CH3—CO—); 2.70 (t, 2H, —CH2—<u>CH2</u>—CO); 3.27 (q, 2H, —NH—CH2—CH2—); 3.66 (s, 2H, —S—CH-2—CO—); 6.72 (s, intensity <1, H—C=C—); 8.23 (t, 1H, —<u>NH</u>—CH2—CH2—); 9.0 (br s, 1H, —N<u>H</u>—C=C—).

B: 2-[N-(S-Acetyl-mercaptoacetyl)-β-alanyl]amino, 3-ethyl, maleic acid anhydride 14b β-hydroxy,β-ethyl, aspartic acid 12b (2.17 g, 12 mmoles was suspended in dimethylformamide (15 ml). Triethylamine (3.41 ml, 25 mmoles) was added whereupon the mixture was heated at 100° C. for 5 minutes to obtain a clear solution.

The solution was cooled to ambient temperature, after which SATA-β-Ala-ONP 8 (4.0 g, 12 mmoles) in dimethylformamide was added. The reaction mixture was stirred for 16 hours. Isolation and purification by column chromatography was carried out as described for compound 9 to give 3.96 g (89%) of 13b. TLC: Rf=0.30.

1H-NMR (6d-DMSO, δ in ppm): 0.74 (t, 3H, CH3—CH2—); 1.52 (q, 2H, CH3—<u>CH2</u>—); 2.38 (t, 2H, —CH2—<u>CH2</u>—CO—); 2.34 (s, 3H, <span style="text-decoration:overline">CH3</span>—CO—); 3.23 (q, 2H, —<u>NH</u>—CH2—CH2—); 3.56 (s, 2H, —S—CH-2—CO—); 4.88 (d, 1H, —NH—CH—COOH); 8.05 (2H, —<u>NH</u>—CH—COOH and —N<u>H</u>—CH2—CH2—).

Aspartic acid derivative 13b was treated with acetic anhydride as described for 13a to give 14b in quantitative yield.

1H-NMR (6d-DMSO, δ in ppm): 1.04 (t, 3H, CH3—CH2—); 2.48 (q, 2H, CH3—<u>CH2</u>—); 2.64 (t,2H, —CH2—<u>CH2</u>—CO—); 2.34 (s, 3H,<span style="text-decoration:overline">CH3</span>—CO—); 3.28 (q, 2H, —<u>NH</u>—CH2—CH2—); 3.56 (s, 2H, —S—CH-2—CO—); 8.22 (t, 1H,—<u>NH</u>—CH2—CH2—); 10.5 (br s,—NH—C=C—).

FABMS (glycerol) m/z 329 (MH+); C13H16O6N2S requires 328.33

C: 2-[N-(S-Acetyl-mercaptoacetyl)-β-alanyl]amino,3-n-propyl, maleic acid anhydride 14c β-Hydroxy,β-n-propyl,aspartic acid 12c (0.293 g; 1.53 mmoles) and triethylamine (0.43 ml); 3.06 mmoles) were heated in dimethylformamide (2 ml) until a clear solution was obtained. At room temperature SATA-β-Ala-ONp 8 (0.50 g; 1.53 mmoles) was added. The mixture was stirred for 3 hours. Isolation and purification of aspartic acid derivative 13c was done as described for compound 9. The yield of 13c was 0.46 g (79%). TLC: Rf=0.38.

1H-NMR (6d-DMSO, δ in ppm): 0.85 (t, 3H, CH3—CH2—CH2—); 1.37 (m, 2H, CH3—<u>CH</u>

2—CH2—); 1.67 (br, t, 2H,CH3—CH2—CH2—); 2.29 (t, 2H, —CH2—CH2—CO—); 2.37 (s, 3H,CH3—CO—); 3.24 (q, 2H, —NH—CH2—CH2—); 3.57 (s, 2H,—S—CH2—CO—); 4.56 (d,11Hz, 1H, —NH—CH—COOH); 7.96 (d,1H, —NH—CH—COOH); 8.08(t, 1H, —NH—CH2—CH2—).

Compound 13c (0.3 g) was cyclized and dehydrated by acetic acid anhydride treatment to give 14c (93%).

1H-NMR (6d-DMSO, δ in ppm): 0.85 (t, 3H, CH3—CH2—CH2—); 1.46 (m, 2H, CH3—CH2—CH2—); 2.48 (t, 2H, CH3—CH2—CH2—); 2.63 (t,2H, —CH2—CH2—CO—); 2.34 (s, 3H, CH3—CO—); 3.27 (q,2H, —NH—CH2—CH2—); 3.57(s,2H,—S—CH2—CO—); 8.25 (t, 1H,—NH—CH2—CH2—); 10.6 (br s, —NH—C=C—)

D: 2-[N-(S-Acetyl-mercaptoacetyl)-β-alanyl]amino, 3-isobutyl, maleic acid anhydride 14d β-Hydroxy,β-isobutyl,aspartic acid 12d (0.314 g; 1.53 mmoles) was acylated with SATA-β-Ala-ONp 8 (0.5 g; 1.53 mmoles) using the method described above to give 0.444 g (74%) of aspartic acid derivative 13d. TLC: Rf=0.44.

FABMS (glycerol) m/z: 393 (MH+); $C_{15}H_{24}N_2O_8S$ requires 392.4.

Acetic anhydride treatment of 13d (0.40 g) gave maleic anhydride derivative 14d in 96% yield (0.35 g).

1H-NMR (6d-DMSO, δ in ppm): 0.83 (t, 6H,(CH3)2CH—CH2—); 1.79 (m, 1H, (CH3)2CH—CH2—); 2.67 (t,2H, —CH2—CH2—CO—); 2.37 (s, 3H, CH3—CO—); 3.27 (q, 2H, —NH—CH2—CH2—); 3.57 (s,2H,—S—CH2—CO—); 8.20 (t, 1H, —NH—CH2—CH2—); 10.6 (br s, —NH—C=C—).

FABMS (glycerol) m/z 357 (MH+); $C_{15}H_{20}N_2O_6S$ requires 356.4.

E: N-(S-acetyl-mercaptoacetyl)β-alanyl-aspartic acid anhydride 14e

The title compound is a bifunctional reagent, lacking the maleic acid double bond, designed to allow preparation of reference conjugates between drug and protein, in which the linkage is through a stable amide bond, as opposed to the labile maleamic acid bonds that are obtained with reagents 10 and 14a-d.

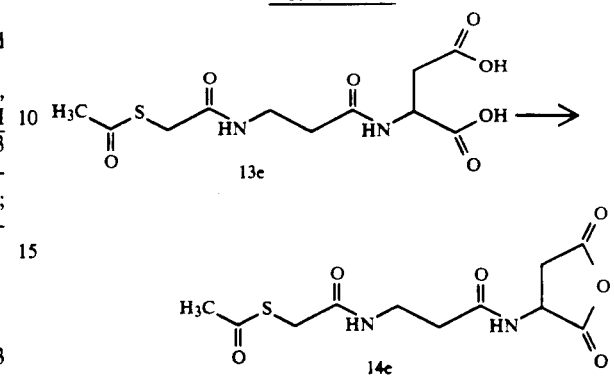

Scheme VI

L-Aspartic acid (0.408 g; 3.06 mmoles) was acylated in dimethylformamide (7 ml) solution with SATA-β-Ala-ONp 8 (1.0 g; 3.06 mmoles) in the presence of triethylamine (0.64 ml; 4.6 mmoles). Isolation and purification of the reaction product 13e by silica chromatography were carried out as described for compound 9. Yield of SATA-β-Ala-Asp-OH was 61% (0.59 g). TLC: Rf=0.38 FABMS (glycerol) m/z 321 (MH+); $C_{11}H_{16}N_2O_7S$ requires 320.3

Aspartic acid derivative 13e (0.34 g) was heated in acetic anhydride (5 ml) at 100° C. for 60 minutes. Solvents were removed by evaporation in vacuo, followed by coevaporation in vacuo with toluene (three times), to afford the aspartic acid anhydride derivative 14e as a yellowish syrup.

FABMS (glycerol) m/z 303 (MH+); $C_{11}H_{14}N_2O_6S$ requires 302.3.

EXAMPLE 7

Derivatization of adriamycin with the bifunctional linker reagent 10 (Scheme VII)

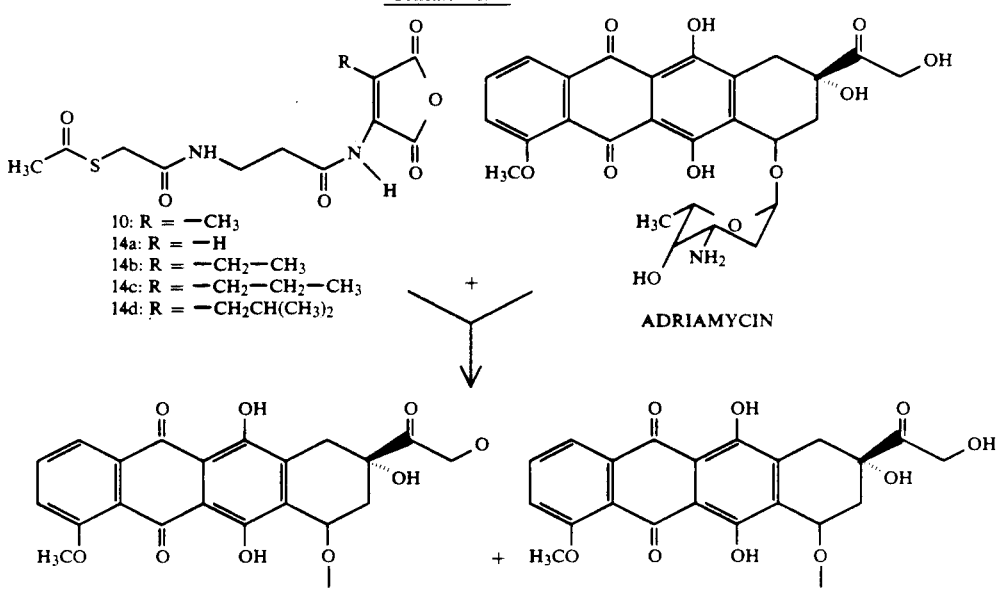

Scheme VII

-continued
Scheme VII

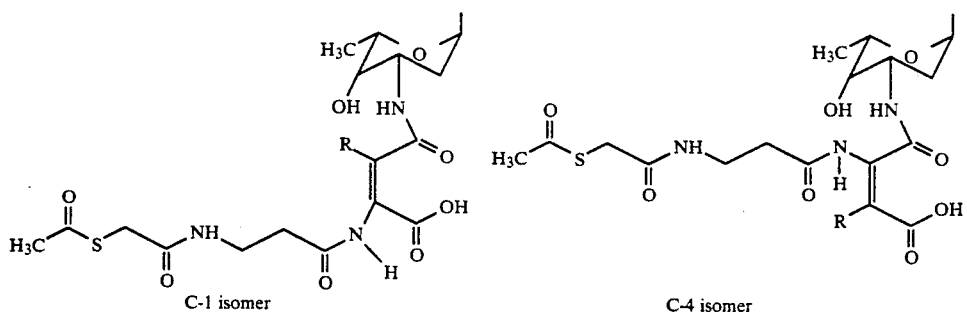

C-1 isomer

C-4 isomer

Adriamycin.HCl (275 mg; 0.47 mmoles) was suspended in N,N-dimethylformamide (2.0 ml). N-ethyl diisopropylamine (248 μl); 1.42 mmoles) and a solution of the maleic anhydride reagent 10 (179 m; 0.57 mmoles) in N,N-dimethylformamide (1.0 ml) were successively added. A clear solution was obtained within 2 minutes. Cold (0° C.) ethyl acetate (40 ml) was slowly added to the reaction mixture while stirring, upon which the product precipitated. The precipitate was isolated by centrifugation and subsequently washed 2 times with ethyl acetate and finally with diethylether and dried (325 mg; 80%).

$^1$H-NMR (DMSO, D$^6$) confirmed the presence of the linker structure, the two possible isomeric structures being present in an approximate 1:2 ratio.

B. Derivatization of adriamycin with the bifunctional linker reagents 14a–e (Schema VII)

Using the experimental conditions described above under A., adriamycin was reacted with the bifunctional reagents 14a–e (Schema V and VI) to yield adriamycin-linker derivatives differing in the substituent at the maleamic acid double bond. For convenience these products will be referred to as: H-linker derivative (obtained through 14a), methyl-linker derivative (obtained through 10), ethyl-linker derivative (obtained through 14b), propyl-linker derivative (obtained through 14c), isobutyl-linker derivative (obtained through 14d), stable-linker derivative (obtained through 14e). The adriamycin-linker derivatives were in each instance obtained as a mixture of two isomeric structures, the result of reaction of the daunosamine amino group at either the C-1 or the C-4 carbonyl site of the anhydride part of the linker reagents.

The adriamycin-linker derivatives were characterized by $^1$H-NMR, FABMS and thin layer chromatography. Analytical data are gathered in Table I.

TABLE I

| Adriamycin linker derivative | Yield | TLC[1] Rf | Isomer[2] Ratio | FABMS (DMSO) positive mode | |
|---|---|---|---|---|---|
| H | 76% 354 mg | 0.53 | 2.5:1 | 866 MNa+ | C$_{38}$H$_{41}$N$_3$O$_{17}$S (843.8) |
| methyl | 80% 325 mg | 0.40 | 2:1 | 880 MNa+ 902 MNa$_2$—H+ | C$_{39}$H$_{43}$N$_3$O$_{17}$S (857.83) |
| ethyl | 87% 154 mg | 0.43 | 3.5:1 | 894 MNa+ 910 MK+ | C$_{40}$H$_{45}$N$_3$O$_{17}$S (871.86) |
| propyl | 83% 412 mg | 0.67 | 4:1 | 908 MNa+ | C$_{41}$H$_{47}$N$_3$O$_{17}$S (885.89) |
| isobutyl | 86% 434 mg | 0.56 | 4:1 | 922 MNa+ 944 MNa$_2$—H+ | C$_{42}$H$_{49}$N$_3$O$_{17}$S (899.9) |
| stable | 80% 651 mg | 0.38 | 3.5:1 | 868 MNa+ 884 MK+ | C$_{38}$H$_{43}$N$_3$O$_{17}$S |

[1] thin layer chromatography on silica 60 F254 ("Merck") in solvent system: dichloromethane-methanol-water-triethylamine (70:30:5:0.1; v/v). The Rf value of the main isomer is given.
[2] isomer ratio: C$_1$/C$_4$ or C$_4$/C$_1$ as estimated from $^1$H-NMR spectra.

EXAMPLE 8

Conjugation of the adriamycin-linker derivative to human serum albumin (HSA) (Scheme VIII)

Scheme VIII

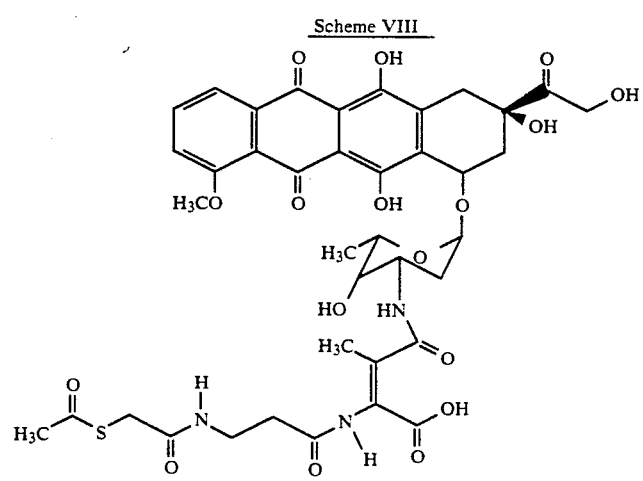

-continued
Scheme VIII

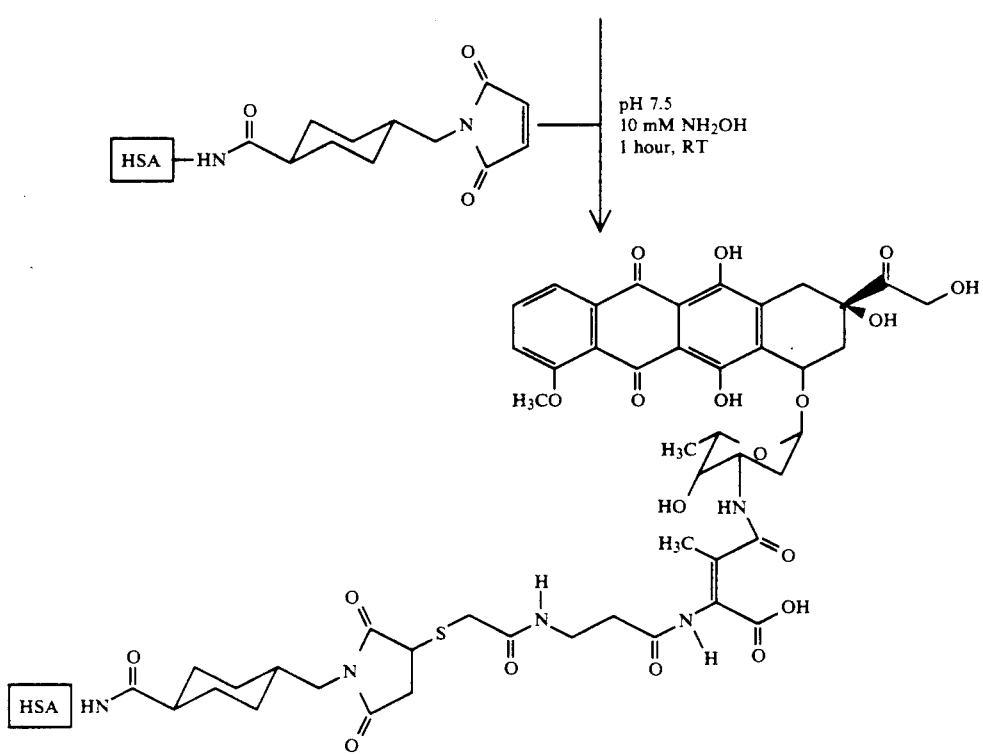

A solution of adriamycin linker derivative (119 mg), described in example 7, in dimethylformamide (2.0 ml) was added to a solution (30 ml) of maleoylated HSA (13 mg/ml; 16 maleimido groups per mole of HSA), prepared as described in example 4A. 0.5M hydroxylamine (1.04 ml), buffered at pH 7.0, was added to the stirred mixture.

The solution was kept at room temperature for 15 minutes and then for 15 hours at 4° C. Isolation of the HSA-adriamycin conjugate was done by successive chromatography on Sephadex LH-20 and on Sephadex G-50, as described in Example 4B. The substitution ratio was found to be 15.8±0.5 moles of adriamycin per mole of HSA, in the final conjugate. The figure is based on the amount of β-alanine in the conjugate as determined by amino acid analyses.

Using the procedure as described above, the h-, the methyl-, the ethyl-, the propyl-, the isobutyl- and the stable (Asp)-linker derivatives of adriamycin (described in Example 7B) were conjugated to human serum albumin, that was previously substituted with maleimido-functions using N-succinimidyl-4-(N-maleimidomethyl)-cyclohexane-1-carboxylate (SMCC).

Table II summarizes data from amino acid analyses on a number of different adriamycin-linker-HSA preparations. The data indicate that the coupling reactions between the thiol group in the adriamycin-linker-derivatives and the maleimido-groups on HSA proceed in an approximate quantitative manner. The data further indicate that the chromatographic methods (Sephadex LH-20 and Sephadex G-50) applied were effective in removing the excess of unbound adriamycin-derivatives from the conjugates.

TABLE II

Composition of Adriamycin-linker-HSA conjugates

| Linker structure | molar ratio: adriamycin/HSA[1] | molar ratio: maleimido groups/HSA[1,2] |
|---|---|---|
| H | 16.3 | 16.4 |
|  | 11.6 | 10.8 |
| methyl | 18.2 | 15.2 |
|  | 11.6 | 10.8 |
|  | 15.8 | 16.0 |
|  | 15.1 | 15.3 |
|  | 12.2 | 10.7 |
| ethyl | 16.6 | 15.8 |
|  | 16.9 | 15.9 |
|  | 13.6 | 14.8 |
|  | 15.9 | 16.0 |
| propyl | 17.0 | 15.9 |
|  | 15.6 | 15.4 |
|  | 14.7 | 15.9 |
| stable (Asp) | 17.0 | 16.2 |
|  | 16.7 | 15.9 |
|  | 15.7 | 16.2 |
|  | 14.4 | 16.5 |
|  | 16.4 | 14.2 |
|  | 14.4 | 17.1 |
| isobutyl | 13.3 | 14.6 |

[1] Adriamycin/HSA molar ratio, determined by amino acid analyses as the number of β-alanine residues per mole of human serum albumin (norleucine was added before hydrolysis as an internal standard).
[2] Maleimido groups (introduced on HSA using SMCC)/HSA molar ratio, determined by amino acid analyses as the number of 4-(aminomethyl)-cyclohexane carboxylic acid residues per mole of human serum albumin.

EXAMPLE 9

Cytotoxicity assay

A human ovarian cell line, $A_{2780}$, was cultured in Roux flasks in Medium 505. For each experiment cells were trypsinised and suspended in medium to a final concentration of $2 \times 10^4$ cells per ml. One hundred μl of the cell suspension was pipetted into each well of a microtitration plate and the plates were left for 16 h. at 37° C. in order to obtain maximal adherence. After one change of fresh medium a dilution series of adriamycin (ADR) and HSA-ADR conjugate, in which the drug was linked to the protein moiety through the methyl-substituted maleamic acid structure, was added to the cells. Incubation was performed for 1 to 7 days at pH 6.0 and 7.3 at 37° C. under standard cell culture conditions. At the end of the incubation period, 50 μl of 1 g/l MTT in medium without FCS was added to each well and incubation was continued for 4 h. Subsequently, the medium was carefully removed, plates were blotted dry and the formazan crystals formed in the cells were dissolved into 100 μl of DMSO. After thorough shaking, absorbance at 570 nm was read in a Titertek Multiskan. From the curves obtained the $ID_{50}$'s ($ID_{50}=50\%$ mortality of the treated cells) for the individual experimental conditions were derived. The results are shown in FIG. 3.

The $ID_{50}$ of HSA-ADR at pH 6.0 is identical to that of free ADR after one week of incubation at pH 6.0, indicating a T½ of 2-3 days for this type of pH-labile linker. The $ID_{50}$ of HSA-ADR at pH 7.5 changes from 0.14 to 0.11 μg/ml. It corresponds with a T½ of around 10 days at this pH.

In the same manner as described above the stable linker HSA-Adriamycin conjugate was tested and compared with the hydrogen and the methyl derivatized linker (FIG. 4).

Also tested and compared were the methyl, ethyl and propyl derivatized linkers in HSA-Adriamycin conjugates (FIG. 5).

Finally, in FIG. 6 the testing and comparison of the methyl and isobutyl linkers is shown.

EXAMPLE 10

This example describes the application of bifunctional reagents according to the present invention on anguidine and verrucarin A, members of the family of trichothecens, mycotoxins with extremely high cytotoxicity.

A: Maleamic acid derivatives of anguidine (Scheme IX) 3-O-(α-aminoisobutyryl) anguidine 16

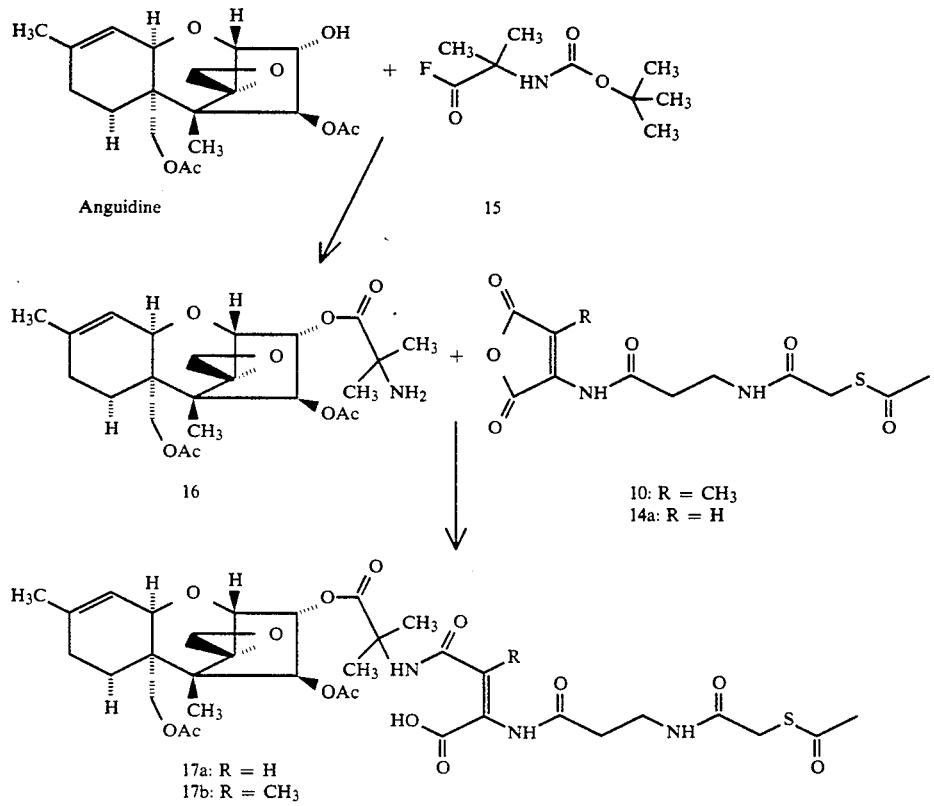

To a solution of anguidine (diacetoxyscirpenol; 72 mg; 0.2 mmoles; purchased from Sigma Chem. Comp.) in dry dichloromethane (1.0 ml) were successively added N-(tert-butyloxycarbonyl)α-aminoisobutyryl fluoride (Boc-Aib-F; 80.6 mg; 0.4 mmoles; prepared from N-(tert-butyloxycarbonyl)α-aminoisobutyric acid, Boc-Aib-OH, and cyanuric fluoride according to a literature method: Tet. Letters 32, 1303—1306, 1991), 1,5-diazabicyclo[4.3.0]non-5-ene (DBN, 0.2 mmoles) and triethylamine (0.4 mmole). The reaction mixture was stirred for 1 hour at ambient temperature, whereupon the solvent as removed in vacuo. The title compound 16 was obtained in 85% yield (77 mg) following chromatography on silica (solvent system: dichloromethane-methanol=97.5:2.5).

1H-NMR (CDCl3): 1.41 ppm (ds, 6H, CH3(Aib)); 3.90 (d, 1H, J=5 Hz, H-2); 4.15 (dd (AB), 2H, J=12 Hz, H-15); 5.13 (dd, 1H, J=5 Hz,H-4); 5.79 (d, 1H, J=3 Hz, H-3). FABMS (glycerol) m/z 452 (MH+); $C_{23}H_{33}NO_8$ requires 451.22.

3-O-[N-(S-Acetyl-mercaptoacetyl)-β-Alanyl-dehydroAspartyl-aminoisobutyryl]anguidine
(3-O-(Sata-βAla-dehydroAsp-Aib)anguidine) 17a To a solution of H-Aib-anguidine 16 (30 mg; 66 μmoles) in dimethylformamide (0.40 ml) were successively added N,N-diisopropyl, N-ethylamine (12 μl, 66

μmoles) and maleic anhydride reagent 14a (20 mg; 66 μmoles). The mixture was stirred at ambient temperature for 30 minutes and subsequently added slowly to cold diethylether while stirring. The precipitate of the product 17a was collected by filtration, washed thrice with diethylether and dried in vacuo (33 mg; 66%).

1H-NMR (CDCl3): 1.58 (ds, 6H, CH3 (Aib)); 2.40 (s, 3H, CH3—CO—S—); 3.54 (s, 2H, CO—CH2—S—); 5.16 (dd, 1H, J=5 Hz,H-4); 5.75 (d, 1H, J=3 Hz, H-3); 7.04 (s, 1H, HC=C). FABMS m/z 752 (MH+); $C_{34}H_{45}N_3O_{14}S$ requires 751.26.

3-O-[N-(S-Acetyl-mercaptoacetyl)-β-Alanyl-β-methyl, dehydroAspartyl-aminoisobutyryl]anguidine (3-O-(Sata-βAla-β-CH3,dehydroAsp-Aib)anguidine) 17b To a solution of H-Aib-anguidine 16 (28 mg; 62 μmoles) in dichloromethane (1.0 ml) were successively added N,N-diisopropyl, N-ethylamine (11 μl; 62 μmoles) and maleic anhydride reagent 10 (20 mg; 66 μmoles). The mixture was stirred for 30 minutes at ambient temperature.

The crude reaction product was purified by chromatography on silica (solvent system: dichloromethane-methanol-N,N-diisopropyl,N-ethylamine (80:20:2) to give the title compound 17b (16.1 mg; 35%)

1H-NMR (CDCl3): 1.38 (s, 3H, CH3(Aib)); 1.41 (s, 3H, CH3(Aib)); 1.48 (s, 3H, CH3—C=C); 2.37 (s, 3H, CH3—CO—S—); 3.58 (s, 2H, S—CH2—CO—); 5.15 (dd, 1H, J=5 Hz, H-4); 5.76 (d, 1H, J=3 Hz, H-3).

B. Maleamic acid derivatives of verrucarin A (Scheme X)

The trichothecene verrucarin A contains a single hydroxyl function at the 2'-position of the macrocyclic ring structure. Using the reaction conditions described under A for anguidine, verrucarin A was reacted with Boc-Aib-F 15 to give the 2'-O-(α- aminoisobutyryl)-derivative 18 (27 mg; 93% yield following chromatography on silica). Derivative 18 was subsequently acylated with maleic anhydride reagents 10 or 14a, to give maleamic acid derivatives 19a (H-linker derivative) and 19b (methyl-linker derivative), respectively. Both compounds were purified by chromatography on silica in the solvent system dichloromethane-methanol-N,N-diisopropyl,N-ethylamine (90:10:1; v/v). Yield: 19a, 88% (28 mg); 19b, 62% (17 mg).

-continued

Scheme X

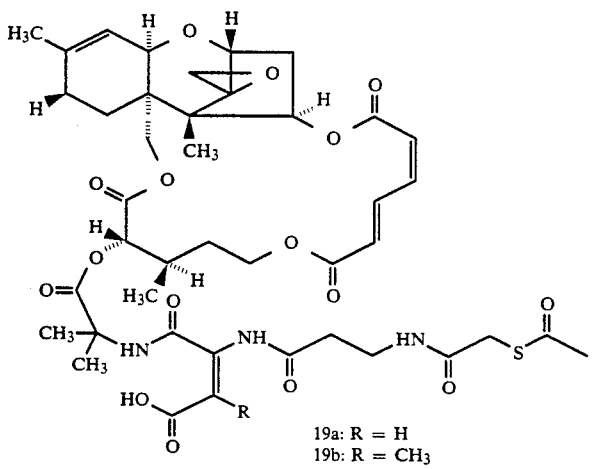

19a: R = H
19b: R = CH₃

Figure 1B:
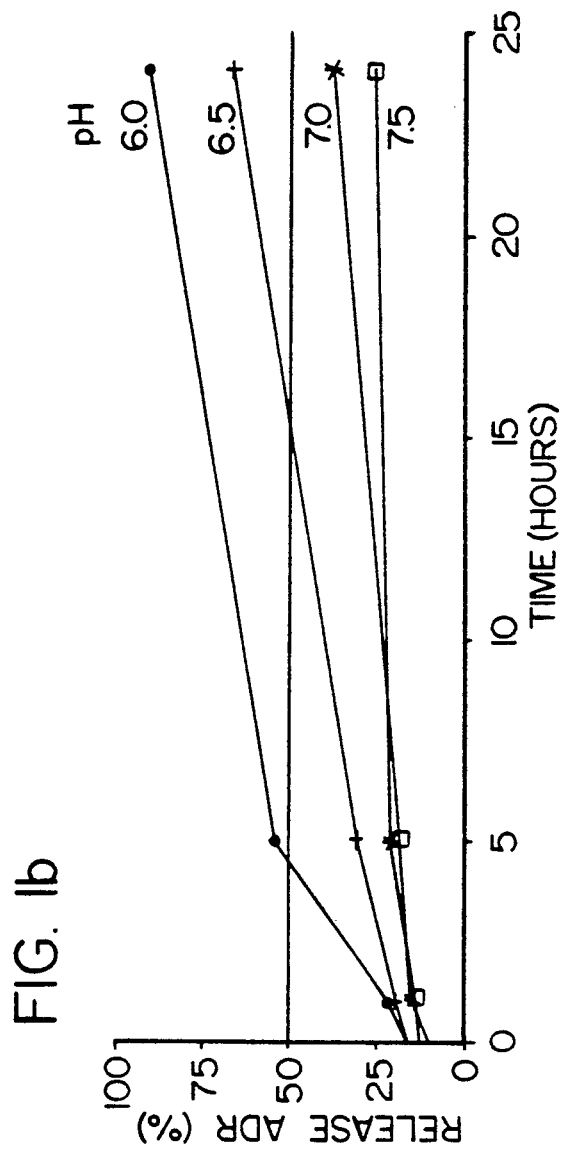
FIG. 1B depicts in graph form the acid sensitivity of the maleamic acid bonds of the invention as indicated by the increased rate of release of adriamycin as the pH of the incubation medium (50 mM phosphate buffer, pH=6.0, 6.5, 7.0 and 7.5, temperature=37° C.) becomes more acidic.
Figure 1C:
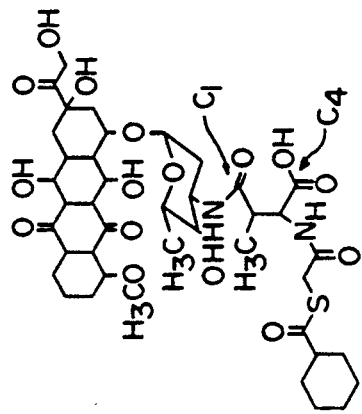
FIG. 1A is an HPLC chromatograph showing that the 2-N-(S-benzoylmercaptoacetyl)amino,3-methyl, maleamic acid derivatives of adriamycin is an approximate 1:1 mixture of the two possible isomeric structures, containing either a C-1 or a C-4 amide linkage (sites are indicated in the structure formula of FIG. 1C of the adriamycin derivative, SBTA-(β-methyl)-dehydro-Asp-ADR).
Figure 1A:
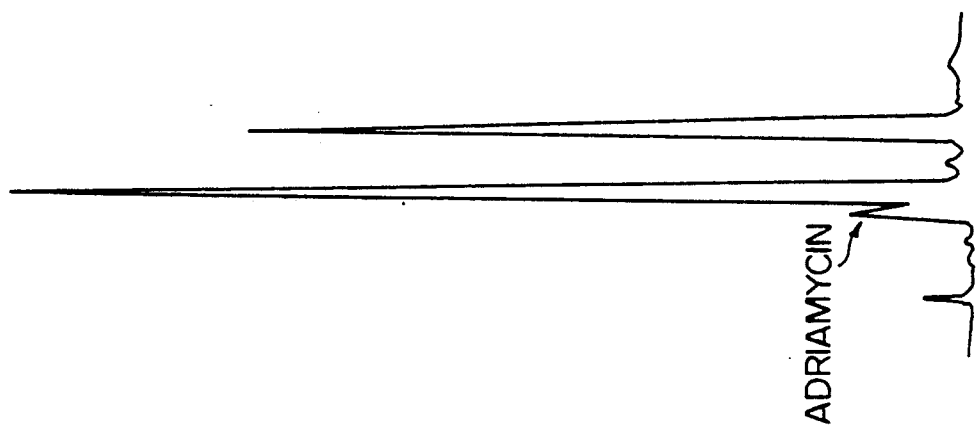
Figure 2:
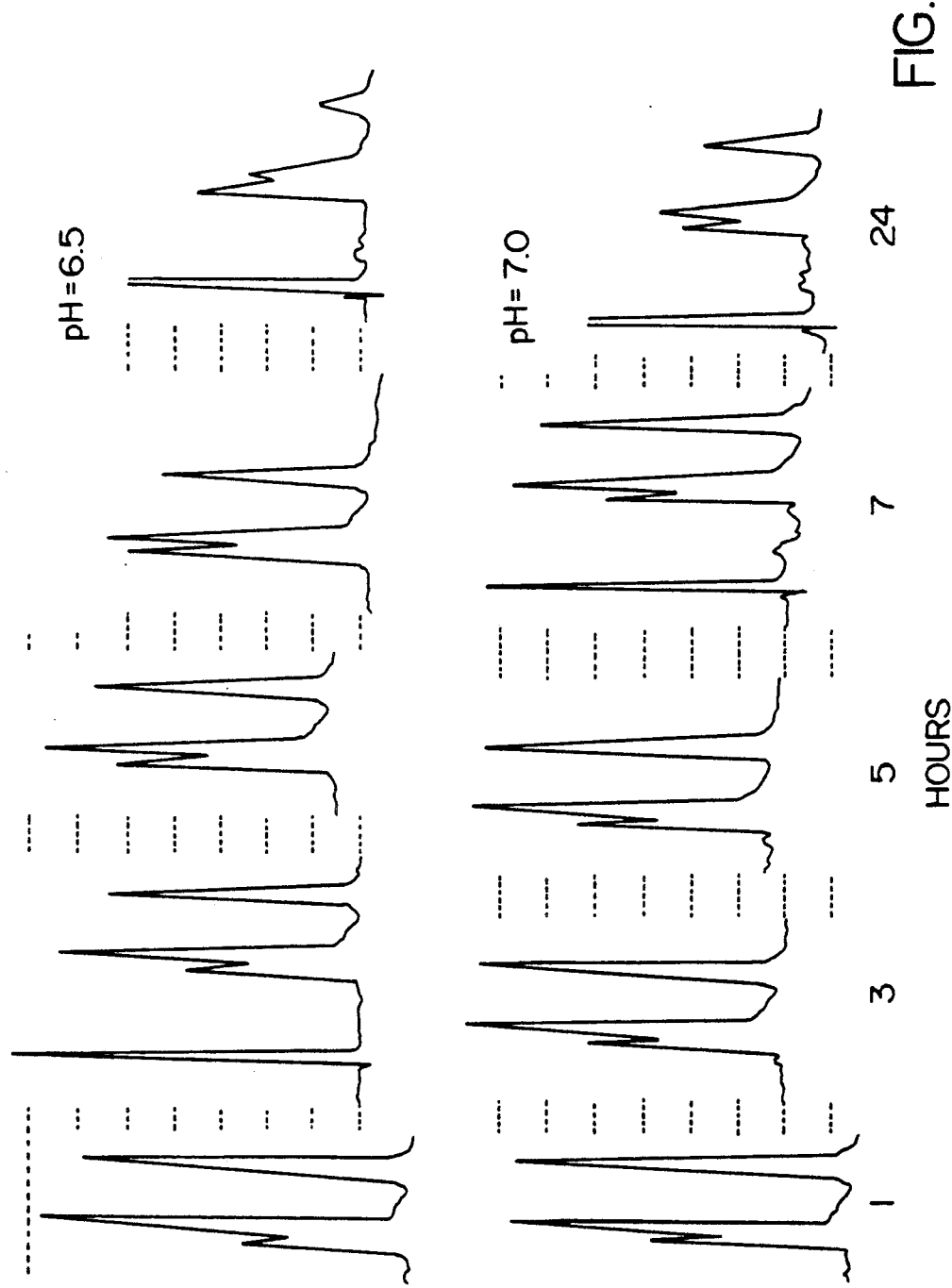
FIG. 2 depicts a series of HPLC chromatographs showing the differential rates of release of adriamycin from a methyl-substituted maleamic acid derivative at pH 6.5 and 7.0 (phosphate buffer, 37° C.), the analyses being performed after 1, 3, 5, 7 and 24 hours. The graphs also indicate the two isomeric structures to have an approximate equal sensitivity towards hydrolysis. These graphs representing raw data were used to construct the graph in FIG. 1B.
Figure 3:
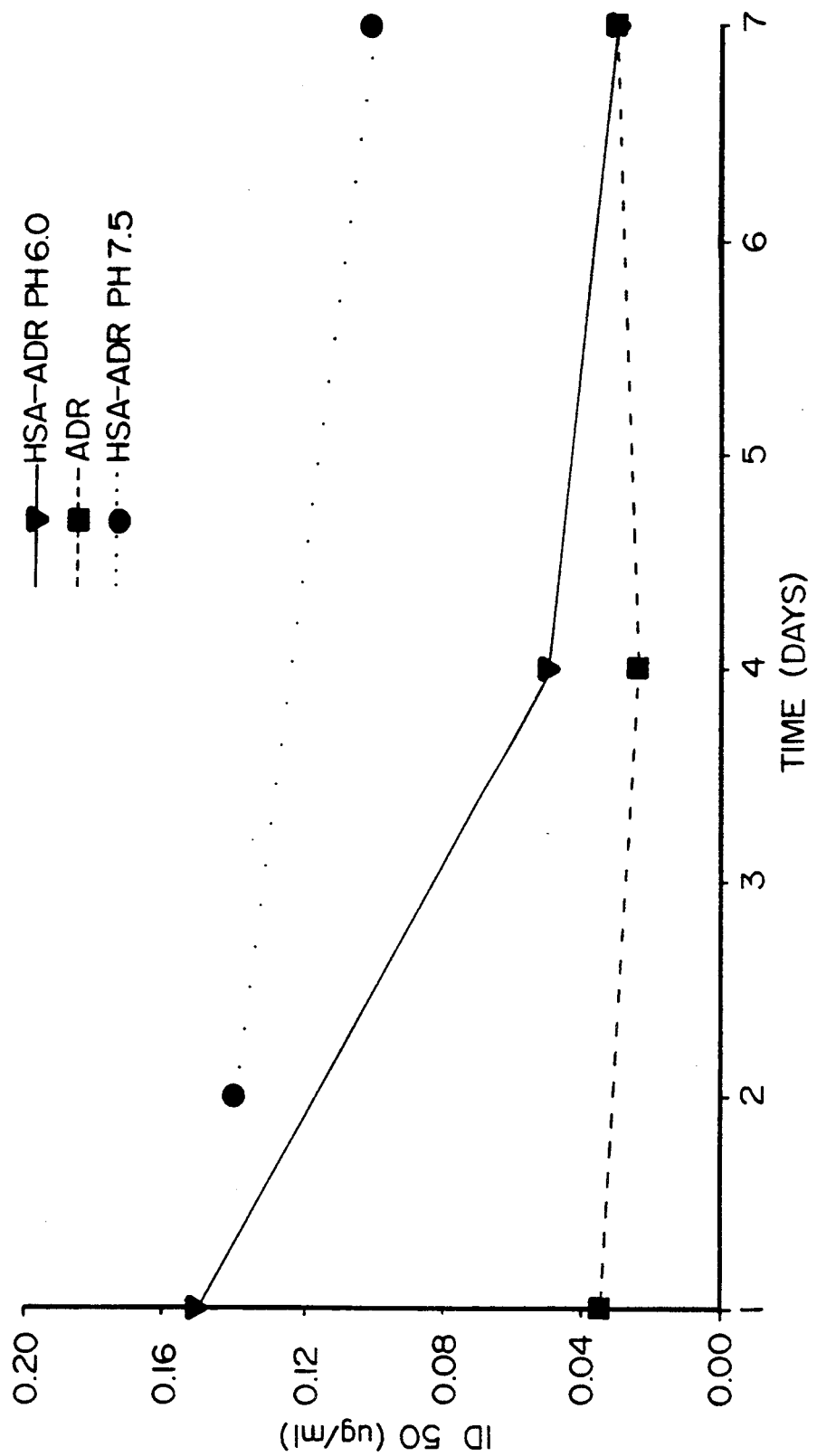
FIG. 3 is a graph showing the ID₅₀ of cells treated with adriamycin (ADR) and HSA-ADR conjugates at pH. 6.0 and 7.5.
Figure 4:
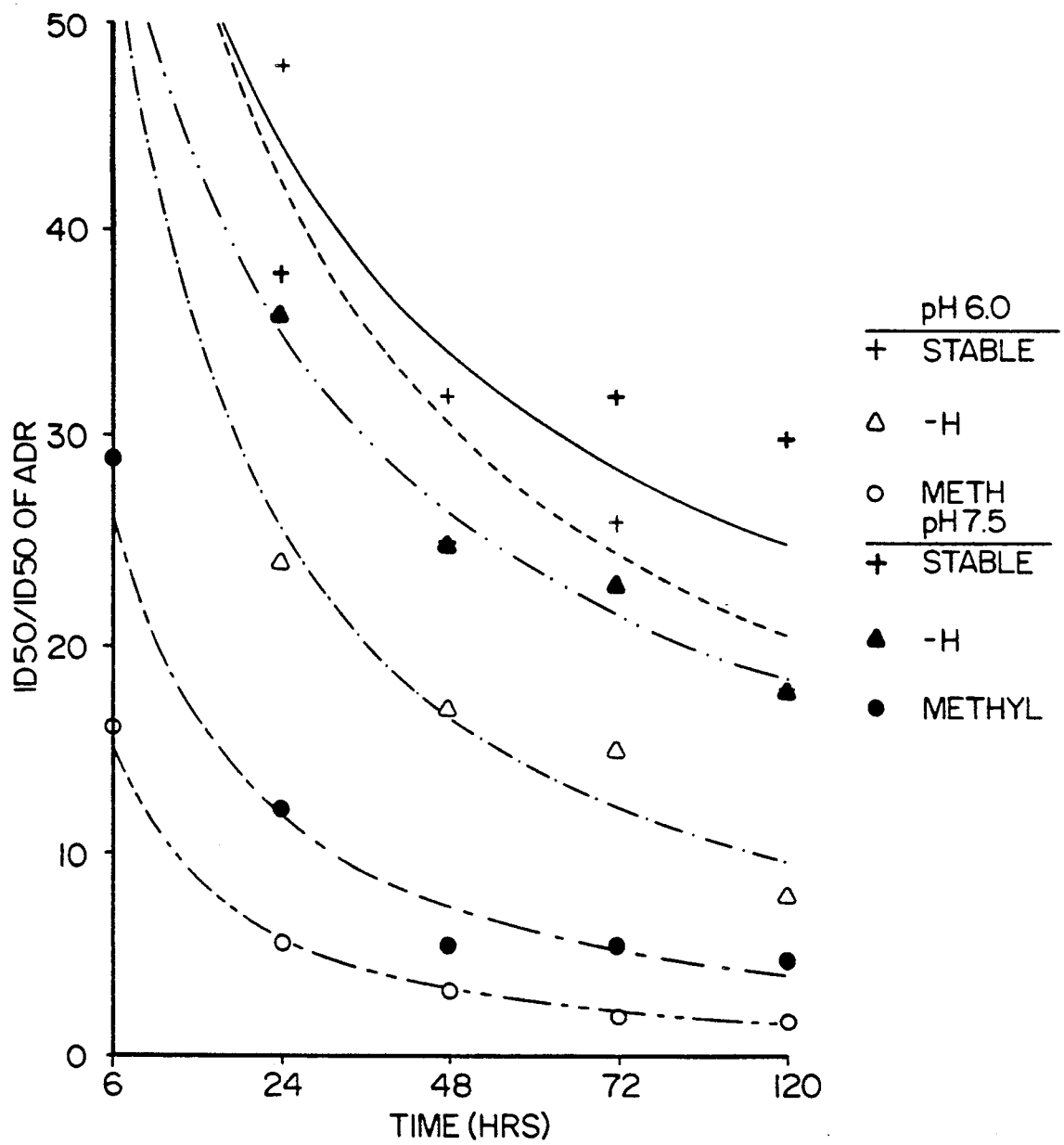
FIG. 4 is a graph showing the ID₅₀ of cells treated with HSA-ADR conjugate and hydrogen and methyl derivatized linkers.
Figure 5:
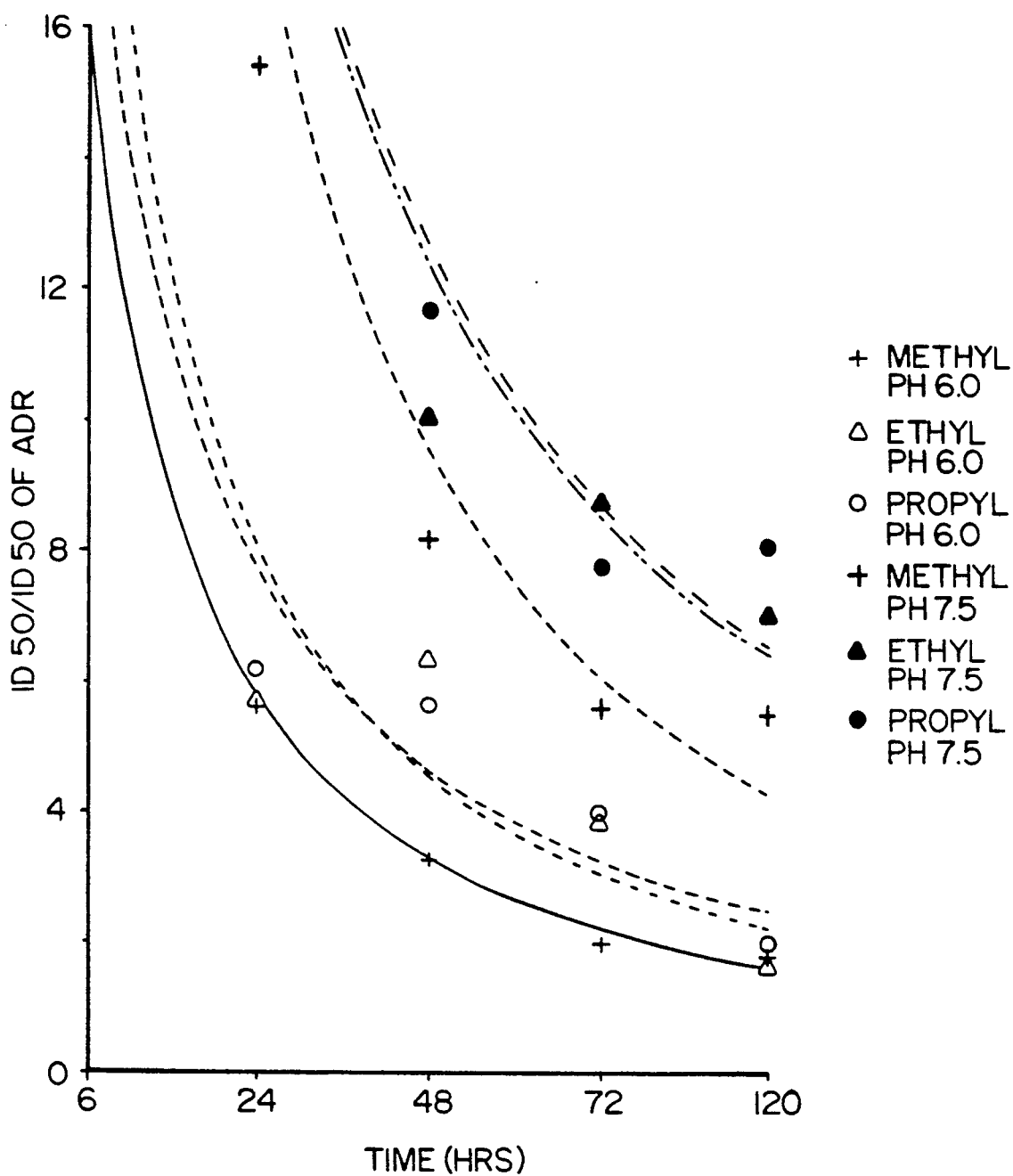
FIG. 5 is a graph as above showing the methyl, ethyl and propyl derivatives linkers in HSA-ADR conjugates.
Figure 6:
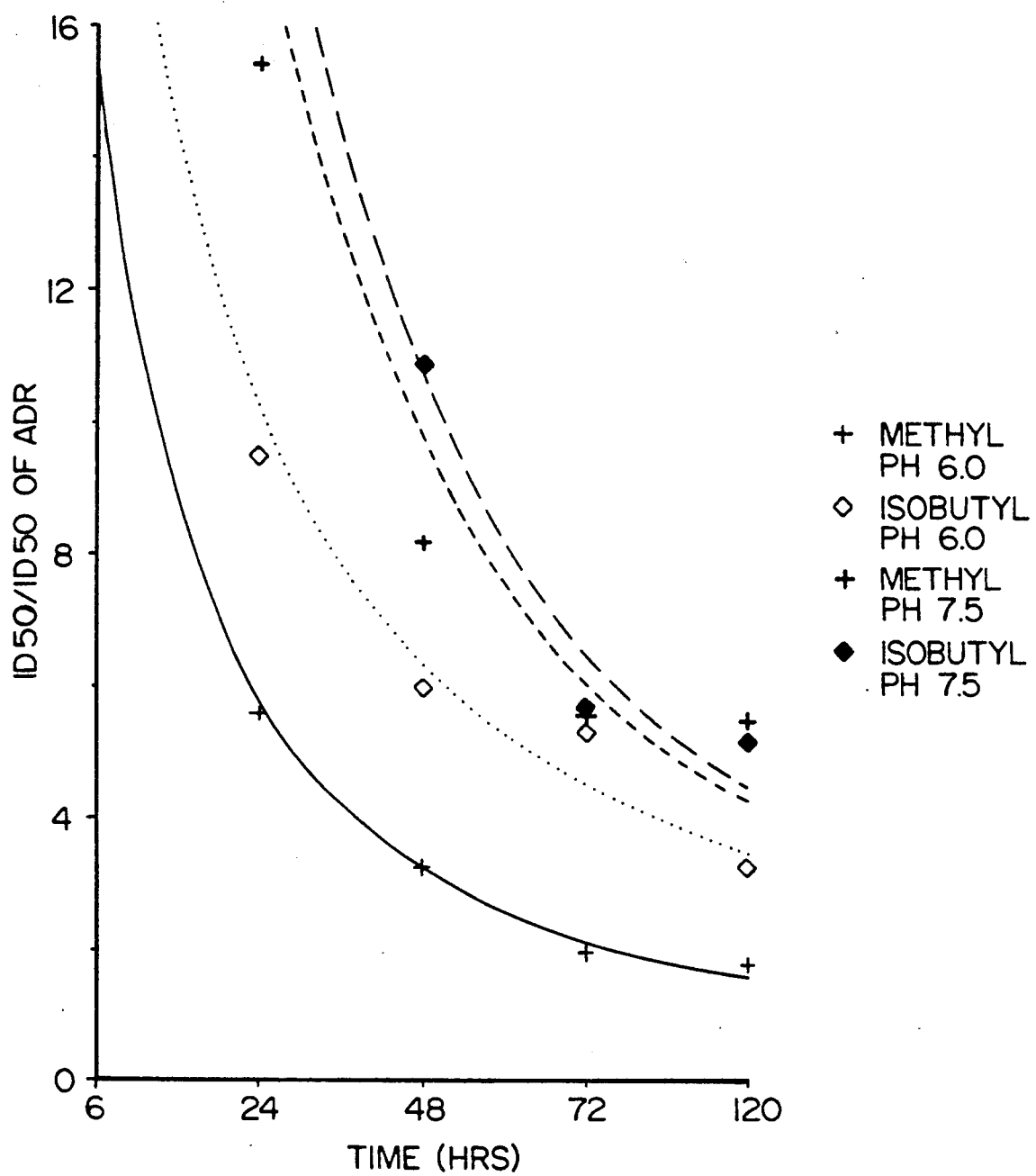
FIG. 6 is a graph as above showing methyl and isobutyl linkers.

We claim:

1. A hydrolytically labile conjugate comprising an acylated active substance having a nucleophilic reactive group according to the general formula:

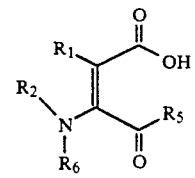

wherein
$R_1$ is selected from the group consisting of H, lower alkyl, —N— lower alkyl, —O—lower aralkyl, —S—lower aralkyl, —N—lower alkylene, —O—lower alkylene, —S—lower alkylene, —N— aryl, —O— aryl, and —S— aryl;
$R_2$ is selected from the group consisting of H, lower alkyl, lower aralkyl and aryl;
$R_5$ is the acylated active substance and
$R_6$ is selected from the group consisting of

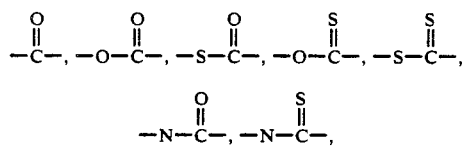

and another chemical structure which is able to delocalize the lone pair electrons of the nitrogen; wherein $R_6$ is coupled with a carrier selected from the group consisting of a proteinaceous substance, an antibody, an antibody fragment, a polymer, and a nucleic acid.

2. A conjugate according to claim 3, wherein the carrier is a serum albumin.

3. A conjugate according to claim 1, wherein the active substance is a cytotoxic agent.

4. A conjugate according to claim 1, wherein the active substance is selected from the group consisting of adriamycin, anguidine and verrucarin A.

5. A conjugate according to claim 1, wherein $R_1$ is methyl, $R_2$ is H, $R_6$ is

and R$_4$ is a pendant reactive group through which R$_6$ is linked to a carrier selected from the group consisting of a proteinaceous substance, an antibody, an antibody fragment, a polymer and a nucleic acid.

6. A conjugate according to claim 1, wherein R$_1$ is ethyl, R$_2$ is H, R$_6$ is

and R$_4$ is a pendant reactive group through which R$_6$ is linked to a carrier selected from the group consisting of a proteinaceous substance, an antibody, an antibody fragment, a polymer and a nucleic acid.

7. A conjugate according to claim 1, wherein R$_1$ is isopropyl, R$_2$ is H, R$_6$ is

and R$_4$ is a pendant reactive group through which R$_6$ is linked to a carrier selected from the group consisting of a proteinaceous substance, an antibody, an antibody fragment, a polymer and a nucleic acid.

8. A conjugate according to claim 1, wherein R$_1$ and R$_2$ and H, R$_6$ is

and R$_4$ is a pendant reactive group through which R$_6$ is linked to a carrier selected from the group consisting of a proteinaceous substance, an antibody, an antibody fragment, a polymer and a nucleic acid.

9. A conjugate according to claim 1, wherein R$_1$ is isobutyl, R$_2$ is H, R$_6$ is

and R$_4$ is a pendant reactive group through which R$_6$ is linked to a carrier selected from the group consisting of a proteinaceous substance, an antibody, an antibody fragment, a polymer and a nucleic acid.

10. A conjugate according to claim 1, wherein R$_1$ is H, R$_2$ is methyl, R$_6$ is

and R$_4$ is a pendant reactive group through which R$_6$ is linked to a carrier selected from the group consisting of a proteinaceous substance, an antibody, an antibody fragment, a polymer and a nucleic acid.

11. A conjugate according to claim 1, wherein R$_1$ is H, R$_2$ is ethyl, R$_6$ is

and R$_4$ is a pendant reactive group through which R$_6$ is linked to a carrier selected from the group consisting of a proteinaceous substance, an antibody, an antibody fragment, a polymer and a nucleic acid.

12. A pharmaceutical composition comprising a conjugate according to claim 1.

13. A hydrolytically labile conjugate comprising an acylated active substance having a nucleophilic reactive group according to the general formula:

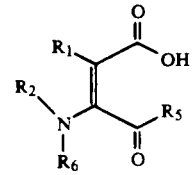

wherein
R$_1$ is selected from the group consisting of H, lower alkyl, —N— lower alkyl, —O—lower aralkyl, —S—lower aralkyl, —N—lower alkylene, —O— lower alkylene, —S—lower alkylene, —N— aryl, —O— aryl, and —S— aryl;
R$_2$ is selected from the group consisting of H, lower alkyl, lower aralkyl and aryl;
R$_5$ is the acylated active substance and
R$_6$ is selected from the group consisting of

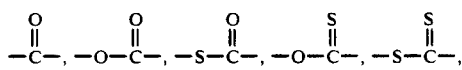

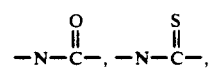

and another chemical structure which is able to delocalize the lone pair electrons of the nitrogen; wherein R$_6$ is coupled with a carrier selected from the group consisting of a proteinaceous substance, an antibody, an antibody fragment, a polymer, and a nucleic acid.

14. A conjugate to claim 13, wherein the active substance is selected from the group consisting of anguidine, adriamycin and verrucarin A.

15. A conjugate according to claim 13, wherein R$_1$ is methyl, R$_2$ is H, R$_6$ is

and R$_4$ is a pendant reactive group through which R$_6$ is linked to a carrier selected from the group consisting of a proteinaceous substance, an antibody, an antibody fragment, a polymer and a nucleic acid.

16. A conjugate according to claim 13, wherein R$_1$ is ethyl, R$_2$ is H, R$_6$ is

and R$_4$ is a pendant reactive group through which R$_6$ is linked to a carrier selected from the group consisting of a proteinaceous substance, an antibody, an antibody fragment, a polymer and a nucleic acid.

17. A conjugate according to claim 13, wherein R$_1$ is isopropyl, R$_2$ is H, R$_6$ is

and $R_4$ is a pendant reactive group through which $R_6$ is linked to a carrier selected from the group consisting of a proteinaceous substance, an antibody, an antibody fragment, a polymer and a nucleic acid.

18. A conjugate according to claim 13, wherein $R_1$ and $R_2$ are H, $R_6$ is

and $R_4$ is a pendant reactive group through which $R_6$ is linked to a carrier selected from the group consisting of a proteinaceous substance, an antibody, an antibody fragment, a polymer and a nucleic acid.

19. A conjugate according to claim 13, wherein $R_1$ is isobutyl, $R_2$ is H, $R_6$ is

and $R_4$ is a pendant reactive group through which $R_6$ is linked to a carrier selected from the group consisting of a proteinaceous substance, an antibody, an antibody fragment, a polymer and a nucleic acid.

20. A conjugate according to claim 13, wherein $R_1$ is H, $R_2$ is methyl, $R_6$ is

and $R_4$ is a pendant reactive group through which $R_6$ is linked to a carrier selected from the group consisting of a proteinaceous substance, an antibody, an antibody fragment, a polymer and a nucleic acid.

21. A conjugate according to claim 13, wherein $R_1$ is H, $R_2$ is ethyl, $R_6$ is

and $R_4$ is a pendant reactive group through which $R_6$ is linked to a carrier selected from the group consisting of a proteinaceous substance, an antibody, an antibody fragment, a polymer and a nucleic acid.

22. A conjugate according to claim 13, wherein the carrier is a serum albumin.

23. A conjugate according to claim 13, wherein the active substance is a cytotoxic agent.

24. A pharmaceutical composition comprising a conjugate according to claim 1.

* * * * *